United States Patent
Moltzen et al.

(10) Patent No.: US 6,596,722 B2
(45) Date of Patent: Jul. 22, 2003

(54) PIPERIDINE, TETRAHYDROPYRIDINE AND PIPERAZINE DERIVATIVES, THEIR PREPARATION AND USE

(75) Inventors: Ejner Knud Moltzen, Gentofte (DK); Christian Krog-Jensen, København (DK); Berith Bjørnholm, Vaerløse (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/901,585

(22) Filed: Jul. 9, 2001

(65) Prior Publication Data
US 2002/0035113 A1 Mar. 21, 2002

Related U.S. Application Data

(63) Continuation of application No. PCT/DK00/00026, filed on Jan. 21, 2000.

(30) Foreign Application Priority Data

Jan. 22, 1999 (DK) .......................... 1999 00084

(51) Int. Cl.[7] ..................... C07D 411/14; C07D 409/14; C07D 405/14; A61K 31/496; A61P 25/24
(52) U.S. Cl. ............... 514/252.13; 514/254.11; 544/376; 544/377
(58) Field of Search ................ 544/377, 373, 544/376; 514/254.11, 254.09, 253.11, 252.13

(56) References Cited

U.S. PATENT DOCUMENTS

| | | | |
|---|---|---|---|
| 5,002,948 A | 3/1991 | Perregaard et al. ......... 514/254 |
| 5,194,437 A | * 3/1993 | Peglion et al. ............... 514/254 |
| 5,464,834 A | * 11/1995 | Peglion et al. ......... 514/252.13 |

FOREIGN PATENT DOCUMENTS

| | | | |
|---|---|---|---|
| EP | 0376607 A1 | 7/1990 | ......... C07D/209/14 |
| EP | 0490772 A1 | 6/1992 | ......... C07D/319/18 |
| EP | 0526434 A1 | 2/1993 | ......... C07D/235/26 |
| EP | 0624584 A1 | 11/1994 | ......... C07D/403/08 |
| EP | 0633260 A1 | 1/1995 | ......... C07D/405/12 |
| WO | 9413659 A1 | 6/1994 | ......... C07D/319/18 |

OTHER PUBLICATIONS

Peglion et al. Characterization of potent and selective antagonists at postsynaptic 5–HT 1A receptors in a series of N–4 substituted arylpiperazines. J. Med. Chem. 38, 4044–4055, 995. Abstract.*

Millan et al. Pro–and antinociceptive actions of seratonin (5–HT) 1A aganists and antagonists in rodents: Relationship to algesiometric paradigm. Behav. Brain Res. 73, 69–77, 1995. Abstract.*

* cited by examiner

Primary Examiner—John M. Ford
Assistant Examiner—Thomas McKenzie
(74) Attorney, Agent, or Firm—Darby & Darby

(57) ABSTRACT

A piperidine, tetrahydropyridine or piperazine derivative having formula (I),

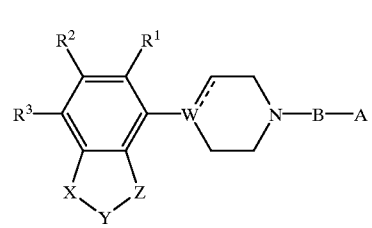

(I)

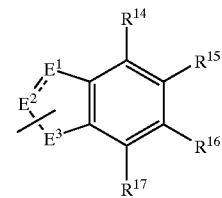

(Ia)

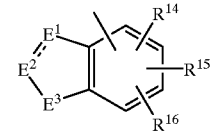

(Ib)

any of its enantiomers or any mixture thereof, or an acid addition salt thereof, wherein B is $C_{1-10}$-alkylene, $C_{1-10}$-alkenylene or $C_{1-10}$-alkynylene; X is —O—, —S—, or $CR^4R^5$—; and Y is —$CR^6R^7$—, —$CR^6R^7$—$CR^8R^9$—, or $CR^6$=$CR^7$—; or X and Y together form a group —$CR^4$=$CR^5$—, or —$CR^4$—$CR^5$—$CR^6R^7$-; Z is —O—, or —S—; W is N, C, or CH, and the dotted line is an optional bond; A is a bicyclic ring selected from (Ia) or (Ib) wherein $E^1$, $E^2$ and $E^3$ are selected from O, S, N, $NR^{11}$, C, $CR^{12}$ and $CHR^{13}$, and the dotted line indicates an optional bond, provided that $E^2$ and $E^1$ and/or $E^3$ may not simultaneously be O, or S. The compounds of the invention are considered useful for the treatment of affective disorders, such as depression, psychosis, anxiety disorders including general anxiety disorder, panic disorder, obsessive compulsive disorder, and eating disorders.

19 Claims, No Drawings

PIPERIDINE, TETRAHYDROPYRIDINE AND PIPERAZINE DERIVATIVES, THEIR PREPARATION AND USE

This is a continuation of international Application No. PCT/DK00/00026, filed Jan. 21, 2000.

The present invention relates to novel piperidine, tetrahydropyridine and piperazine derivatives which are potent serotonin reuptake inhibitors, pharmaceutical compositions containing these compounds and the use thereof for the treatment of disorders or diseases responsive to the inhibition of serotonin re-uptake. The compounds of the invention also possess antagonistic activity at $5\text{-HT}_{1A}$ receptors and are considered to be particularly useful for the treatment of depression.

BACKGROUND

Selective serotonin (or 5-HT) reuptake inhibitors (SSRIs) such as fluoxetine, paroxetine, sertraline, fluvoxamine and citalopram represent a major step forward in the treatment of depression because they have fewer and less severe side effects compared to first generation antidepressant (tricyclics and non-selective MAO inhibitors). The side effects associated with first generation antidepressants are such that they cause some patients to withdraw from treatment.

SSRIs and all other antidepressants currently available suffer from a serious drawback in that several weeks of treatment are necessary to produce the therapeutic effect. The late onset of action is a significant problem, particularly in the treatment of patients with severe depression and suicide potential. Further, one in three patients are not responsive to SSRIs.

Electrophysiological experiments in rats have shown that acute administration of SSRIs reduces firing of 5-HT neurons of dorsal raphe nucleus in the rodent brain, whereas sustained treatment with SSRIs leads to normalization of the firing activity of the 5-HT neurons (Arborelius, L. et al. *Naunyn-Schmiedeberg's Arch. Pharmacol.* 1995, 352, 157; Gartside, S. E. et al. *Br. J. Pharmacol.* 1995, 115, 1064: Chaput, Y. et al. *Naunyn-Schmiedeberg's Arch. Pharmacol.* 1986, 33, 342).

Further, it has been shown that the recovery of the firing activity of 5-HT neurons is linked to desensitization of somatodendritic $5\text{-HT}_{1A}$ autoreceptors (Le Poul, E. et al, *Naunyn-Schmiedeberg's Arch. Pharmacol.* 1995, 352, 141; Invernizzi, R. et al, *Eur. J. Pharmacol.* 1994, 260, 243).

It has thus been suggested that simultaneous administration of SSRIs and an agent causing rapid desensitization or inhibition of the $5\text{-HT}_{1A}$ receptor mediated feed back mechanism would lead to rapid onset of antidepressive effect (Artigas, F. et al, *Trends Neurosci.* 1996, 19, 378; De Vry, J., et al, *Drug News Perspec.* 1996, 9, 270).

The effect of combined administration of a compound that inhibits serotonin reuptake and a $5\text{-HT}_{1A}$ receptor antagonist has been evaluated in several studies (Innis, R. B. et al., *Eur. J. Pharmacol.,* 1987, 143, p 195–204 and Gartside, S. E., *Br. J. Pharmacol.* 1995, 115, p 1064–1070, Blier, P. et al, *Trends Pharmacol. Sci.* 1994, 15, 220). In these studies it was found that $5\text{-HT}_{1A}$ receptor antagonists inhibit the decrease in firing caused by acute administration of serotonin reuptake inhibitors.

Further, treatment with a combination of pindolol (a well known $5\text{-HT}_{1A}$ receptor and β-adrenoceptor antagonist) and SSRIs has been evaluated in clinical trials. A remarkable improvement of the mood of patients was reported within one week. In addition, combined administration of pindolol and an SSRI was shown to have a good effect on patients who were non-responsive to treatment with currently available antidepressants (Artigas F. et al., *Arch. Gen. Psychiatry,* 1994, 51, p 248–251 and Blier, P. et al., *J. Clin. Psychopharmacol.* 1995, 15, p 217–222).

Several patent applications have been filed which cover the use of a combination of a $5\text{-HT}_{1A}$ antagonist and a serotonin reuptake inhibitor for the treatment of depression (see EP-A2-687 472 and EP-A2-714 663).

In EP-A1-529 462, certain 1,4-benzodioxan derivatives having the general formula

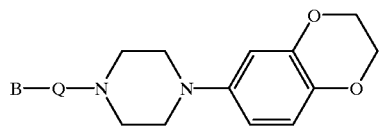

wherein B is an optionally substituted indol-3-yl group and Q is $C_nH_{2n}$ wherein n is 1, 2, 3, 4, 5, or 6 are disclosed. These compounds are said to have serotonin agonistic and serotonin antagonistic activity as well as serotonin reuptake inhibiting activity and to be useful as anxiolytics, antidepressants, antipsychotics, antihypertensives, and cerebroprotective agents.

In U.S. Pat. No. 5,002,948, Perregaard et al. disclose related indoles, indazoles, 2-indolones and 2,3-dihydro derivatives thereof having the formula

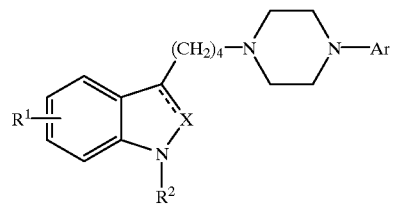

wherein X is —CH—, —CH$_2$—, —NH—, or —CO—; and Ar is

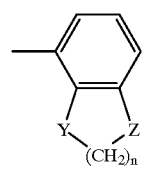

wherein Y is O, or S, Z is O, S, or —CH$_2$—, and n is 1, 2, or 3.

These compounds are valuable $5\text{-HT}_{1A}$ receptor ligands.

OBJECT OF THE INVENTION

It is the object of the present invention to provide compounds with potent serotonin reuptake inhibiting activity as well as antagonistic properties at $5\text{-HT}_{1A}$ receptors. Such compounds may be useful as fast onset of action medicaments for the treatment of affective disorders, such as depression, psychosis, anxiety disorders including general anxiety disorder, panic disorder, obsessive compulsive disorder, and eating disorders.

A further object of the present invention is to provide a pharmaceutical composition comprising the above compounds as active ingredients.

SUMMARY OF THE INVENTION

The invention then, inter alia, comprises the following alone or in combination:

A piperidine, tetrahydropyridine or piperazine derivative having the formula:

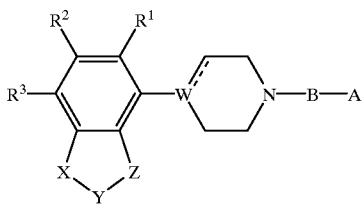

(I)

any of its enantiomers or any mixture thereof, or an acid addition salt thereof, wherein B is $C_{1-10}$-alkylene, $C_{2-10}$-alkenylene or $C_{2-10}$-alkynylene;

X is —O—, —S—, or —$CR^4R^5$—; and

Y is —$CR^6R^7$—, —$CR^6R^7$—$CR^8R^9$—, or —$CR^6$=$CR^7$—; or

X and Y together form a group —$CR^4$=$CR^5$—, or —$CR^4$=$CR^5$—$CR^6R^7$—;

Z is —O—, or —S—;

W is N, C, or CH, and the dotted line is an optional bond;

$R^4$, $R^5$, $R^6$, $R^7$, $R^8$ and $R^9$ are each independently selected from hydrogen, halogen, trifluoromethyl, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, $C_{1-6}$-alkoxy, $C_{1-6}$-alkylthio, amino, $C_{1-6}$-alkylamino, $C_{1-6}$-dialkylamino, phenylamino or phenyl-$C_{1-6}$-alkylamino wherein the phenyl group may be substituted, acylamino, hydroxy, —SH, cyano, nitro, —$COOR^{18}$, —$SO_2$—$R^{19}$ and $C_{1-6}$-alkyl substituted with a substituent selected from halogen, $C_{1-6}$-alkoxy, $C_{1-6}$-alkylthio, amino, $C_{1-6}$-alkylamino, $C_{1-6}$-dialkylamino, acylamino, hydroxy, —SH, cyano, nitro, —$COOR^{18}$ and —$SO_2$—$R^{19}$;

$R^{18}$ is hydrogen, $C_{1-6}$-alkyl, $C_{2-6}$-alkenyl, $C_{2-6}$-alkynyl, phenyl or phenyl-$C_{1-6}$-alkyl wherein the phenyl groups may be substituted, amino, $C_{1-6}$-alkylamino or $C_{1-6}$-dialkylamino, and $R^{19}$ is $C_{1-6}$-alkyl, amino, $C_{1-6}$-alkylamino, $C_{1-6}$-dialkylamino, phenyl or phenyl-$C_{1-6}$-alkyl wherein the phenyl groups may be substituted;

A is a bicyclic ring selected from

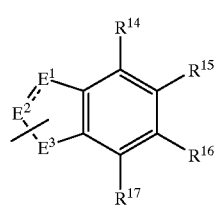

(Ia)

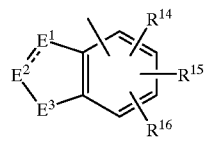

(Ib)

wherein $E^1$, $E^2$ and $E^3$ are selected from O, S, N, $NR^{11}$, C, $CR^{12}$ and $CHR^{13}$, and the dotted line indicates an optional bond, provided that $E^2$ and $E^1$ and/or $E^3$ may not simultaneously be O, or S;

$R^1$, $R^2$, $R^3$, $R^{12}$, $R^{13}$, $R^{14}$, $R^{15}$, $R^{16}$ and $R^{17}$ are each independently selected from hydrogen, halogen, trifluoromethyl, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, $C_{1-6}$-alkoxy, hydroxy, formyl, acyl, amino, $C_{1-6}$-alkylamino, $C_{1-6}$-dialkylamino, acylamino, $C_{1-6}$-alkoxycarbonylamino, aminocarbonylamino, $C_{1-6}$-alkylaminocarbonylamino, $C_{1-6}$-dialkylaminocarbonylamino, nitro, cyano and —$SO_2$—$R^{19}$, wherein $R^{19}$ is $C_{1-6}$-alkyl, amino, $C_{1-6}$-alkylamino, $C_{1-6}$-dialkylamino, phenyl, or phenyl-$C_{1-6}$-alkyl wherein the phenyl groups may be substituted;

$R^{11}$ is selected from hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, phenyl or phenyl-$C_{1-6}$-alkyl wherein the phenyl group may be substituted, acyl, formyl and —$SO_2$—$R^{19}$, wherein $R^{19}$ is $C_{1-6}$-alkyl, amino, $C_{1-6}$-alkylamino, $C_{1-6}$-dialkylamino, phenyl or phenyl-$C_{1-6}$-alkyl wherein the phenyl groups may be substituted;

provided that at least one of $R^4$–$R^9$ is different from hydrogen when A is a group of formula (If)

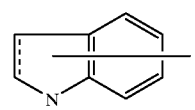

(If)

In one embodiment, the present invention relates to a compound wherein A is selected from the groups of formula (Ic), (Id) and (Ie)

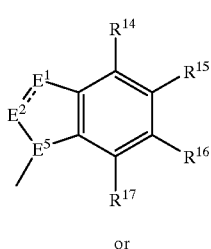

(Ic)

or (Id)

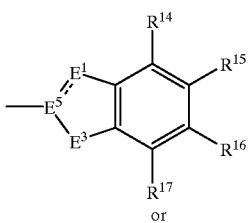

or (Ie)

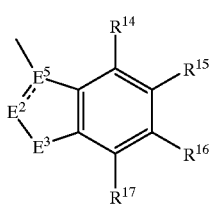

wherein $E^1$, $E^2$, $E^3$, and $R^{14}$, $R^{15}$, $R^{16}$ and $R^{17}$ are as defined in claim 1 and $E^5$ is N, C or $CR^{12}$.

In a further embodiment, the present invention relates to a compound wherein the bicyclic ring A is selected from the groups (If) to (Iq):

(If)
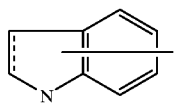

(Ig)
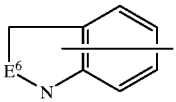

(Ih)
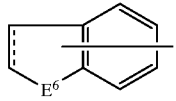

(Ii)
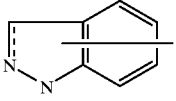

(Ij)
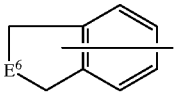

(Ik)
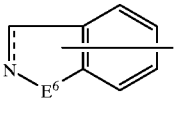

(Im)
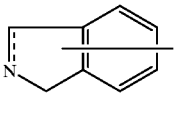

(In)
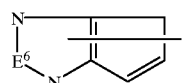

(Io)
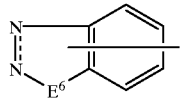

(Ip)
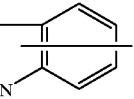

(Iq)
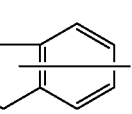

which is attached to the remainder of the compound of formula (I) via a carbon atom or a nitrogen atom in any of the two rings and wherein the dotted line is an optional bond, $E^6$ is O or S, and wherein any of the carbon atoms in the ring may be substituted with any of the substituents defined for $R^{12}$–$R^{17}$ above, and wherein the nitrogen atoms in the ring may be substituted with any of the substituents defined above for $R^{11}$.

In a preferred embodiment, the present invention relates to a compound wherein A is a group of formula (Ih), (Ij) or (Iq).

In a more preferred embodiment, the present invention relates to a compound wherein A is a group of formula (Ih) wherein $E^6$ is preferably O. Such compound is preferably attached to the remainder of the derivative of formula (I) via position 3 in the five-membered ring.

In a further embodiment, the present invention relates to a compound wherein A is a group of formula (If).

In a final embodiment, the present invention relates to a compound wherein

B is $C_{1-6}$-alkylene, $C_{2-6}$-alkenylene, or $C_{2-6}$-alkynylene;

X is —O—, or —S—; and

Y is —$CR^6R^7$—, —$CR^6R^7$—$CR^8R^9$—, or —$CR^6$=$CR^7$—; and

Z is —O—, or —S—;

W is N, C, or CH;

$R^6$, $R^7$, $R^8$ and $R^9$ are each independently selected from hydrogen, halogen, trifluoromethyl, $C_{1-6}$-alkyl, $C_{1-6}$-alkoxy, $C_{1-6}$-alkylthio, amino, $C_{1-6}$-alkylamino, $C_{1-6}$-dialkylamino, phenylamino or phenyl-$C_{1-6}$-alkylamino wherein the phenyl group may be substituted, hydroxy, cyano, nitro, —$COOR^{18}$, —$SO_2$—$R^{19}$ and $C_{1-6}$-alkyl substituted with halogen, $C_{1-6}$-alkoxy, $C_{1-6}$-alkylthio, amino, $C_{1-6}$-alkylamino, $C_{1-6}$-dialkylamino, acylamino, hydroxy, cyano, nitro, —$COOR^{18}$ or —$SO_2$—$R^{19}$;

$R^{18}$ is hydrogen, $C_{1-6}$-alkyl, amino, $C_{1-6}$-alkylamino or $C_{1-6}$-dialkylamino;

$R^{19}$ is $C_{1-6}$-alkyl, amino, $C_{1-6}$-alkylamino or $C_{1-6}$-dialkylamino;

$R^1$, $R^2$, $R^3$, $R^{12}$, $R^{13}$, $R^{14}$, $R^{15}$, $R^{16}$ and $R^{17}$ are each independently selected from hydrogen, halogen, trifluoromethyl, $C_{1-6}$-alkyl, $C_{1-6}$-alkoxy, hydroxy, amino, $C_{1-6}$-alkylamino, $C_{1-6}$-dialkylamino, nitro and cyano; and $R^{11}$ is selected from hydrogen, $C_{1-6}$-alkyl, phenyl or phenyl-$C_{1-6}$-alkyl wherein the phenyl group may be substituted, acyl, formyl and —$SO_2$—$R^{19}$, wherein $R^{19}$ is $C_{1-6}$-alkyl, amino, $C_{1-6}$-alkylamino or $C_{1-6}$-dialkylamino.

Specific compounds of the invention are compounds selected from

1-[1,4-Benzodioxan-5-yl]-4-[1-(inden-1-yl)-4-butyl]piperazine,
1-[1,4-Benzodioxan-5-yl]-4-[1-(indan-1-yl)-1-butene-4-yl]piperazine,
1-[1,4-Benzodioxan-5-yl]-4-[1-(indan-1-yl)-4-butyl]piperazine,
1-[1,4-Benzodioxan-5-yl]-4-[2-(5-fluorobenzofuran-3-yl)ethyl]piperazine,
1-[1,4-Benzodioxan-5-yl]-4-[3-(6-fluorobenzo[1,2]isoxazol-3-yl)-1-propyl]piperazine,
1-[Benzofuran-7-yl]-4-[2-(5-fluorobenzofuran-3-yl)ethyl]piperazine,
1-[1,4-Benzodioxan-5-yl]-4-[2-(6-chloroindazol-3-yl)ethyl]piperazine,
1-[1,4-Benzodioxan-5-yl]-4-[2-(4-methylbenzofuran-3-yl)ethyl]piperazine,
1-[1,4-Benzodioxan-5-yl]-4-[2-(5-chlorobenzofuran-3-yl)ethyl]piperazine,
1-[1,4-Benzodioxan-5-yl]-4-[2-(6-methylbenzofuran-3-yl)ethyl]piperazine,
1-[1,4-Benzodioxan-5-yl]-4-[2-(benzofuran-3-yl)ethyl]piperazine,
1-[2-(5-Chlorobenzofuran-3-yl)ethyl]-4-[2,3-dihydrobenzofuran-7-yl]-1,2,3,6-tetrahydropyridine,
4-[Benzofuran-7-yl]-1-[2-(5-fluorobenzofuran-3-yl)ethyl]-1,2,3,6-tetrahydropyridine,
1-[1,4-Benzodioxan-5-yl]-4-[2-(7-chlorobenzofuran-3-yl)ethyl]piperazine,
1-[1,4-Benzodioxan-5-yl]-4-[3-(7-chlorobenzofuran-3-yl)-1-proyl]piperazine,
1-[8-Cyano-1,4-benzodioxan-5-yl]-4-[3-(7-chlorobenzofuran-3-yl)propyl]piperazine,
1-[1,4-Benzodioxan-5-yl]-4-[3-(7-chloro-4-methylbenzofuran-3-yl)-1-propyl]piperazine,
1-[1,4-Benzodioxan-5-yl]-4-[3-(4-methylbenzofuran-3-yl)-1-propyl]piperazine
1-[1,4-Benzodioxan-5-yl]-4-[2-(6-bromobenzofuran-3-yl)ethyl]piperazine,
1-[1,4-Benzodioxan-5-yl]-4-[3-(4-chlorobenzofuran-3-yl)-1-propyl]piperazine
1-[1,4-Benzodioxan-5-yl]-4-[4-(4-methylbenzofuran-3-yl)-1-butyl]piperazine
1-[1,4-Benzodioxan-5-yl]-4-[4-(4-chlorobenzofuran-3-yl)-1-butyl]piperazine
1-[1,4-Benzodioxan-5-yl]-4-[4-(7-chlorobenzofuran-3-yl)-1-butyl]piperazine
4-[1,4-Benzodioxan-5-yl]-1-[2-(5-fluorobenzofuran-3-yl)ethyl]-1,2,3,6-tetrahydropyridine,
4-[1,4-Benzodioxan-5-yl]-1-[2-(5-fluorobenzofuran-3-yl)ethyl]piperidine,
4-[2-(6-Chloro-1H-indol-3-yl)ethyl]-1-[2-hydroxymethyl-1,4-benzodioxan-5-yl]piperazine,
4-[2-(6-Chloro-1H-indol-3-yl)ethyl]-1-[2-cyano-1,4-benzodioxan-5-yl]piperazine,
4-[2-(6-Chloro-1H-indol-3-yl)ethyl]-1-[2-trifluoromethyl-1,4-benzodioxan-5-yl]piperazine,
4-[2-(6-Chloro-1H-indol-3-yl)ethyl]-1-[2-(ethyl-oxo-carbonyl)-1,4-benzodioxan-5-yl]piperazine,
1-[2-Carbamoyl-1,4-benzodioxan-5-yl]-4-[2-(6-Chloro-1H-indol-3-yl)ethyl]piperazine,
4-[2-(6-Chloro-1H-indol-3-yl)ethyl]-1-[2-(N,N-dimethylcarbamoyl)-1,4-benzodioxan-5-yl]piperazine,
1-[2-Amino-1,4-benzodioxan-5-yl]-4-[2-(6-Chloro-1H-indol-3-yl)ethyl]piperazine,
1-[2-Acetamido-1,4-benzodioxan-5-yl]-4-[2-(6-Chloro-1H-indol-3-yl)ethyl]piperazine,
4-[2-(6-Chloro-1H-indol-3-yl)ethyl]-1-[2-(N,N-dimethylamino)-1,4-benzodioxan-5-yl]piperazine,
4-[2-(6-Chloro-1H-indol-3-yl)ethyl]-1-[2-hydroxymethyl-1,4-benzodioxan-5-yl]tetrahydropyridine,
4-[2-(6-Chloro-1H-indol-3-yl)ethyl]-1-[2-cyano-1,4-benzodioxan-5-yl]tetrahydropyridine,
4-[2-(6-Chloro-1H-indol-3-yl)ethyl]-1-[2-trifluoromethyl-1,4-benzodioxan-5-yl]tetrahydropyridine,
4-[6-Chloro-1H-indol-3-yl)ethyl]-1-[2-(ethyl-oxo-carbonyl)-1,4-benzodioxan-5-yl]tetrahydropyridine,
1-[2-Carbamoyl-1,4-benzodioxan-5-yl]-4-[2-(6-Chloro-1H-indol-3-yl)ethyl]tetrahydropyridine,
4-[2-(6-Chloro-1H-indol-3-yl)ethyl]-1-[2-(N,N-dimethylcarbamoyl)-1,4-benzodioxan-5-yl]tetrahydropyridine,
1-[2-Amino-1,4-benzodioxan-5-yl]-4-[2-(6-Chloro-1H-indol-3-yl)ethyl]tetrahydropyridine,
1-[2-Acetamido-1,4-benzodioxan-5-yl]-4-[2-(6-Chloro-1H-indol-3-yl)ethyl]tetrahydropyridine,
4-[2-(6-Chloro-1H-indol-3-yl)ethyl]-1-[2-(N,N-dimethylamino)-1,4-benzodioxan-5-yl]tetrahydropyridine,
4-[2-(6-Chloro-1H-indol-3-yl)ethyl]-1-[2-hydroxymethyl-1,4-benzodioxan-5-yl]piperidine,
4-[2-(6-Chloro-1H-indol-3-yl)ethyl]-1-[2-cyano-1,4-benzodioxan-5-yl]piperidine,
4-[2-(6-Chloro-1H-indol-3-yl)ethyl]-1-[2-trifluoromethyl-1,4-benzodioxan-5-yl]piperadine,
4-[2-(6-Chloro-1H-indol-3-yl)-1-[2-(ethyl-oxo-carbonyl)-1,4-benzodioxan-5-yl]piperadine,
1-[2-Carbamoyl-1,4-benzodioxan-5-yl]-4-[2-(6-Chloro-1H-indol-3-yl)ethyl]piperadine,
4-[2-(6-Chloro-1H-indol-3-yl)ethyl]-1-[2-(N,N-dimethylcarbamoyl)-1,4-benzodioxan-5-yl]piperidine,
1-[2-Amino-1,4-benzodioxan-5-yl]-4-[2-(6-Chloro-1H-indol-3-yl)ethyl]piperidine,
1-[2-Acetamido-1,4-benzodioxan-5-yl]-4-[2-(6-Chloro-1H-indol-3-yl)ethyl]piperadine,
4-[2-(6-Chloro-1H-indol-3-yl)ethyl]-1-[2-(N,N-dimethylamino)-1,4-benzodioxan-5-yl]piperidine,
1-[2,2-Bis(hydroxymethyl)-1,4-benzodioxan-5-yl]-4-[2-(6-chloro-1H-indol-3-yl)ethyl]piperazine,
4-[2-(6-Chloro-1H-indol-3-yl)ethyl]-1-[2,2-dicyano-1,4-benzodioxan-5-yl]piperazine,
1-[2,2-Bis(trifluoromethyl)-1,4-benzodioxan-5-yl]-4-[2-(6-chloro-1H-indol-3-yl)ethyl]piperazine,
1-[2,2-Bis(ethyl-oxo-carbonyl)-1,4-benzodioxan-5-yl]-4-[2-(6-chloro-1H-indol-3-yl)ethyl]piperazine,
1-[2,2-Bis(hydroxymethyl)-1,4-benzodioxan-5-yl]-4-[2-(6-chloro-1H-indol-3-yl)ethyl]tetrahydropyridine,
4-[2-(6-Chloro-1H-indol-3-yl)ethyl]-1-[2,2-dicyano-1,4-benzodioxan-5-yl]tetrahydropyridine,
1-[2,2-Bis(trifluoromethyl)-1,4-benzodioxan-5-yl]4-[2-(6-chloro-1H-indol-3-yl)ethyl]tetrahydropyridine,
1-[2,2-Bis(ethyl-oxo-carbonyl)-1,4-benzodioxan-5-yl]-4-[2-(6-chloro-1H-indol-3-yl)ethyl]tetrahydropyridine,
1-[2,2-Bis(hydroxymethyl)-1,4-benzodioxan-5-yl-4-[2-(6-chloro-1H-indol-3-yl)ethyl]piperidine,
4-[2-(6-Chloro-1H-indol-3-yl)ethyl]-1-[2,2-dicyano-1,4-benzodioxan-5-yl]piperdine,
1-[2,2-Bis(trifluoromethyl)-1,4-benzodioxan-5-yl]-4-[2-(6-chloro-1H-indol-3-yl)ethyl]piperidine, 1-[2,2-Bis(ethyl-oxo-carbonyl)-1,4-benzodioxan-5-yl]-4-[2-(6-chloro-1H-indol-3-yl)ethyl]piperidine, or a pharmaceutically acceptable acid addition salt thereof.

Particularly preferred compounds are

1-[1,4-Benzodioxan-5-yl]-4-[1-(inden-1-yl)-4-butyl] piperazine,

1-[1,4-Benzodioxan-5-yl]-4-[1-(indan-1-yl)-1-buten-4-yl] piperazine,

1-[1,4-Benzodioxan-5-yl]-4-[1-(indan-1-yl)-4-butyl] piperazine,

1-[1,4-Benzodioxan-5-yl]-4-[2-(5-fluorobenzofuran-3-yl) ethyl]piperazine,

1-[1,4-Benzodioxan-5-yl]-4-[3-(6-fluorobenzo[1,2] isoxazol-3-yl)-1-propyl]piperazine, 1-[Benzofuran-7-yl]-4-[2-(5-fluorobenzofuran-3-yl)ethyl] piperazine, 1-[1,4-Benzodioxan-5-yl]-4-[2-(6-chloroindazol-3-yl)ethyl] piperazine, 1-[1,4-Benzodioxan-5-yl]-4-[2-(4-methylbenzofuran-3-yl) ethyl]piperazine, 1-[1,4-Benzodioxan-5-yl]-4-[2-(5-chlorobenzofuran-3-yl) ethyl]piperazine, 1-[1,4-Benzodioxan-5-yl]-4-[2-(6-methylbenzofuran-3-yl) ethyl]piperazine, 1-[1,4-Benzodioxan-5-yl]-4-[2-(benzofuran-3-yl)ethyl] piperazine, 1-[1,4-Benzodioxan-5-yl]-4-[2-(7-chlorobenzofuran-3-yl) ethyl]piperazine, 1-[1,4-Benzodioxan-5-yl]-4-[3-(7-chloro-4-methylbenzofuran-3-yl)-1-propyl]piperazine, 1-[1,4-Benzodioxan-5-yl]-4-[3-(4-methylbenzofuran-3-yl)-1-propyl]piperazine, 1-[2-(5-Chlorobenzofuran-3-yl)ethyl]-4-[2,3-dihydrobenzofuran-7-yl]-1,2,3,6-tetrahydropyridine, and 4-[Benzofuran-7-yl]-1-[2-(5-fluorobenzofuran-3-yl) ethyl]-1,2,3,6-tetrahydropyridine, or a pharmaceutically acceptable acid addition salt thereof.

The invention also relates to a pharmaceutical composition comprising a compound of formula (I) or a pharmaceutically acceptable salt thereof and at least one pharmaceutically acceptable carrier or diluent In a further embodiment, the invention relates to the use of a compound of formula (I) or a pharmaceutically acceptable acid addition salt thereof for the preparation of a medicament for the treatment of a disorder or disease responsive to the inhibition of serotonin reuptake and antagonism of 5-HT$_{1A}$ receptors.

In particular, the invention relates to the use of a compound according to the invention or a pharmaceutically acceptable acid addition salt thereof for the preparation of a medicament for the treatment of affective disorders, such as depression, psychosis, anxiety disorders including general anxiety disorder, panic disorder, obsessive compulsive disorder, and eating disorders.

In still another embodiment, the present invention relates to a method for the treatment of a disorder or disease of living animal body, including a human, which is responsive to the inhibition of serotonin reuptake and antagonism of 5-HT$_{1A}$ receptors comprising administering to such a living animal body, including a human, a therapeutically effective amount of a compound of formula (I) or a pharmaceutically acceptable acid addition salt thereof.

In particular, the invention relates to a method for the treatment of affective disorders, such as depression, psychosis, anxiety disorders including general anxiety disorder, panic disorder, obsessive compulsive disorder, and eating disorders comprising administering a therapeutically effective amount of a compound of formula (I) or a pharmaceutically acceptable acid addition salt thereof to a living animal body, including a human, in need thereof.

Due to their combined antagonism of 5-HT$_{1A}$ receptors and serotonin reuptake inhibiting effect, the compounds of the invention are considered particularly useful as fast onset of action medicaments for the treatment of depression. The compounds may also be useful for the treatment of depression in patients who are resistant to treatment with currently available antidepressants.

The compounds claimed herein are considered particularly useful for the treatment of depression requiring fast onset of antidepressive effect, or a depression which is resistant to other antidepressants.

Halogen means fluoro, chloro, bromo, or iodo.

$C_{1-6}$-alkyl means a straight or branched chain of one to six carbon atoms, including for example: methyl, ethyl, propyl, isopropyl, butyl, pentyl and hexyl.

$C_{2-6}$-alkenyl means a chain of from two to six carbon atoms containing one double bond, including for example ethenyl, 1-,2-propenyl, 2-,3-propenyl etc.

$C_{2-6}$-alkynyl means a chain of from two to six carbon atoms containing one triple bond, including for example ethynyl, 1-,2-propynyl, 2-,3-propynyl etc.

$C_{1-10}$-alkylene means a chain of one to ten carbon atoms, including for example ethylene, propylene, butylene etc. $C_{1-6}$ alkylene is an alkylene group as defined above with up to 6 carbon atoms.

$C_{2-10}$-alkenylene is a chain of two to ten carbon atoms containing one double bond, including for example ethenylene, propenylene, butenylene etc. $C_{2-6}$ alkenylene is an alkenylene group as defined above containing from 2 to 6 carbon atoms.

$C_{2-10}$-alkynylene is a chain of from two to ten carbon atoms containing one triple bond, including for example ethynylene, propynylene, butynylene etc. $C_{2-6}$ alkynylene is an alkynylene group as defined above containing from 2 to 6 carbon atoms.

$C_{3-7}$-cycloalkyl means cyclic alkyl of from three to seven carbon atoms, including cyclopropyl, cyclobutyl etc.

$C_{3-7}$-cycloalkyl-$C_{1-6}$-alkyl is composed of $C_{3-7}$-cycloalkyl and $C_{1-6}$-alkyl wherein $C_{3-7}$-cycloalkyl and $C_{1-6}$-alkyl is as defined above.

$C_{1-6}$-alkoxy is —O-alkyl where alkyl is as defined above.

$C_{1-6}$-alkylthio is —S-alkyl where alkyl is as defined above.

Acyl means —CO—$C_{1-6}$-alkyl wherein $C_{1-6}$-alkyl is as defined above.

Amino means NH$_2$.

$C_{1-6}$-alkylamino means —NH—$C_{1-6}$-alkyl, and $C_{1-6}$-dialkylamino means —N—($C_{1-6}$-alkyl)$_2$ where $C_{1-6}$-alkyl is as defined above.

$C_{1-6}$-alkoxycarbonylamino means $C_{1-6}$-alkyl-O—CO—NH— wherein $C_{1-6}$-alkyl is as defined above.

$C_{1-6}$-alkylaminocarbonylamino means $C_{1-6}$-alkyl-NH—CO—NH— wherein $C_{1-6}$-alkyl is as defined above.

$C_{1-6}$-dialkylaminocarbonylamino means ($C_{1-6}$-alkyl)$_2$—NH—CO—NH— wherein $C_{1-6}$-alkyl is as defined above.

As used herein a phenyl group which may be substituted means a phenyl group which may be substituted one or more times with a substituent selected form halogen, trifluoromethyl, cyano, nitro, amino, $C_{1-6}$-alkylamino, $C_{1-6}$-dialkylamino, $C_{1-6}$-alkyl, $C_{1-6}$-alkoxy and hydroxy.

Exemplary of organic acid addition salts according to the invention are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of inorganic acid addition salts according to the invention are those with hydrochloric, hydrobromic, sulfuric, sulfamic, phosphoric, and nitric acids. The acid addition salts of the invention are preferably pharmaceutically acceptable salts formed with non-toxic acids.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (i.e. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l-(tartrates, mandelates, or camphorsulphonate) salts for example. The compounds of the present invention may also be resolved by the formation of diastereomeric derivatives.

Additional methods for the resolution of optical isomers, known to those skilled in the art, may be used. Such methods include those discussed by J. Jaques, A. Collet, and S. Wilen in "Enantiomers, Racemates, and Resolutions", John Wiley and Sons, New York (1981).

Optically active compounds can also be prepared from optically active starting materials.

The compounds of the invention can be prepared by one of the following methods comprising:

a) reducing the carbonyl groups of a compound of formula

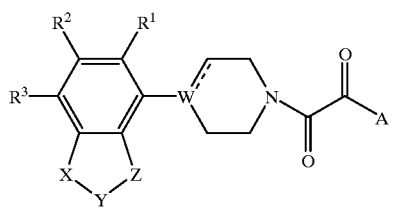

(V)

wherein A, $R^1$–$R^3$, X, Y, Z, W, and the dotted line are as defined above;

b) alkylating an amine of formula

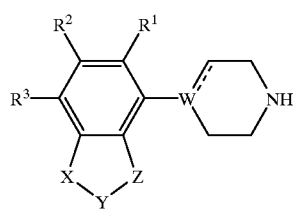

(VI)

wherein $R^1$–$R^3$, X, Y, Z, W, and the dotted line are as defined above with a reagent of formula L—B—A wherein A and B are as defined above and L is a suitable leaving group such as halogen, mesylate, or tosylate;

c) reductive alkylation of an amine of formula

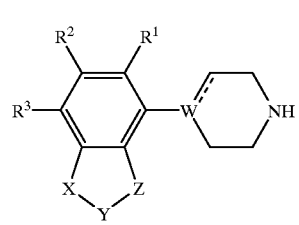

(VI)

wherein $R^1$–$R^3$, X, Y, Z, W, and the dotted line are as defined above with a reagent of formula K—B'—A, wherein A is as defined above, K is either an aldehyde or a carboxylic acid group and B' is such a group, that —CH$_2$—B'— belongs to the groups defined above by B;

d) reducing the double bond of A' of compounds of formula

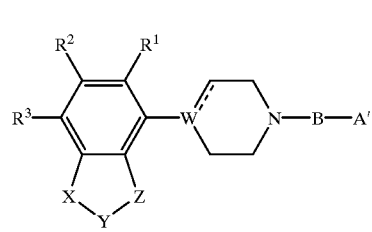

(I)

wherein $R^1$—$R^3$, B, X, Y, Z, W, and the dotted line are as defined above and A' is a group of formula Ia or Ib as defined above in which the dotted line represents a bond, in order to obtain the corresponding 2,3-dihydro derivatives, e.g. 2,3-dihydroindole or 2,3-dihydrobenzofuran;

e) reducing the double bond of the tetrahydropyridines of formula

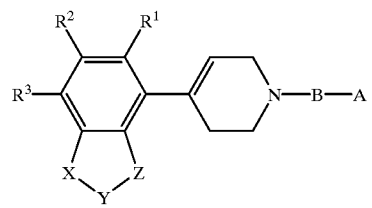

(VIII)

wherein $R^1$–$R^3$, A, B, X, Y, and Z are as previously defined, in order to obtain the corresponding piperidine derivatives;

f) treating a compound of general formula (I) wherein Y is —CR$^6$=CR$^7$—, or wherein X and Y together form a group —CR$^4$=CR$^5$—, or —CR$^4$=CR$^5$—CR$^6$R$^7$ with a reducing agent in order to reduce the double bond, thereby obtaining a corresponding reduced ring system;

g) reductive removal of one or more of the substituents $R^1$–$R^3$ or $R^{12}$–$R^{17}$ in a compound of general formula (I) in which one or more of these substituents are selected from chloro, bromo, or iodo;

h) dialkylating an amine of formula

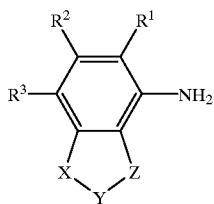
(IX)

wherein $R^1$–$R^3$, X, Y, and Z is as defined above with a reagent of formula

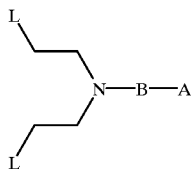
(X)

wherein A and B are as defined above and L is a suitable leaving group such as halogen, mesylate, or tosylate;

i) dialkylating an amine of formula

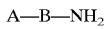
A—B—$NH_2$ (XI)

wherein A is as defined above with a reagent of formula

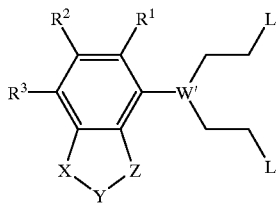
(XII)

wherein $R^1$–$R^3$, X, Y, and Z are as defined above, W' is N or CH, and L is a suitable leaving group such as halogen, mesylate, or tosylate;

j) alkylating or acylating the nitrogen atom of the group A″ in formula XIII,

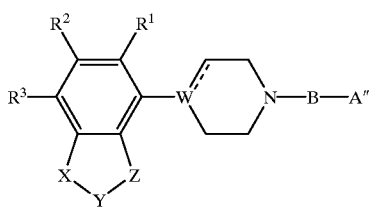
(XIII)

wherein $R^1$–$R^3$, B, X, Y, Z, W, and the dotted line are as defined above, and A″ is a group selected from a group of formula Ia or Ib as defined above in which either $E^1$, $E^2$, or $E^3$ is NH with alkylating or acylating reagents of formula $R^0$—L, wherein L is suitable a leaving group such as halogen, mesylate, or tosylate and $R^0$ is as defined above for $R^{11}$ but not hydrogen;

k) cyclization of compounds of formula XIV,

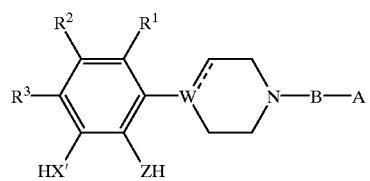
(XIV)

wherein $R^1$–$R^3$, A, B, W, and the dotted line are as defined above and X' is selected from O or S, with dialkylatng reagents of formula L—Y—L, wherein Y is as defined above and L is a suitable leaving group as described above;

l) cyclization of a compound of formula XVa or XVb,

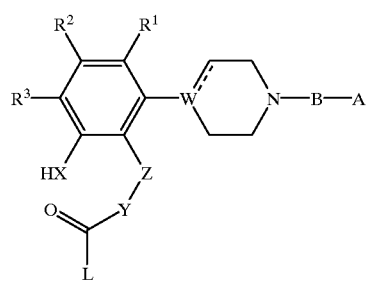
XVa

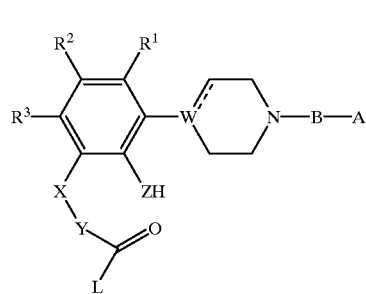
XVb wherein $R^1$–$R^3$, A, B, X, Y, Z, W, and the dotted line are as defined above, and L is a suitable leaving groups as defined above or is an N-imidazolyl or pentafluorophenoxy group in order to obtain the corresponding cyclic oxo-derivatives;

m) cyclocondensation of compounds of formula XVIa or XVIb,

XVIa

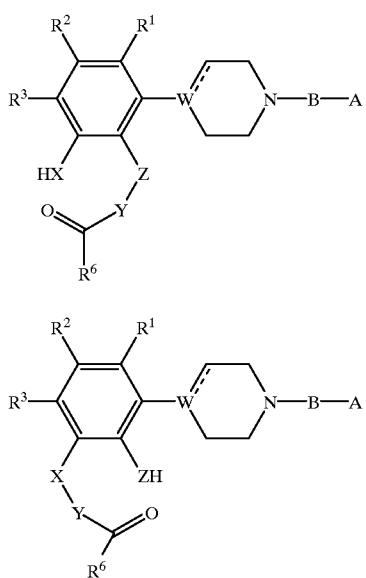

XVIb wherein $R^1$–$R^3$, $R^6$, A, B, X, Y, Z, W, and the dotted line are as defined above in order to obtain the corresponding cyclic hydroxy derivatives, or by successive dehydration to obtain the corresponding unsaturated ring system;

n) substitution of the hydroxyl group in compounds of formula XVII, (XVII)

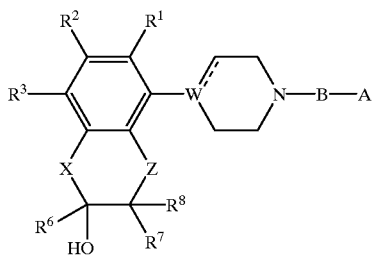

wherein $R^1$–$R^3$, $R^6$–$R^8$, A, B, X, Z, W, and the dotted line are as defined above, with cyanating reagents in order to obtain the corresponding cyano derivatives;

o) hydrolysis or reduction of the cyano group of compounds of formula XVIII, (XVIII)

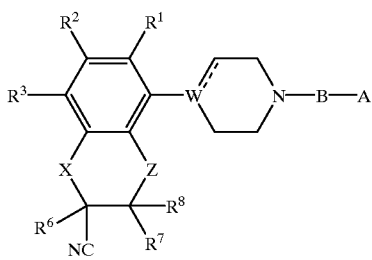

wherein $R^1$–$R^3$, $R^6$–$R^8$, A, B, X, Z, W, and the dotted line are as defined above, in order to obtain the corresponding carboxylic acid derivatives or the corresponding aminoethyl derivatives;

p) Oxidation of the hydroxy alkyl chain in compounds of formula XIX, (XIX)

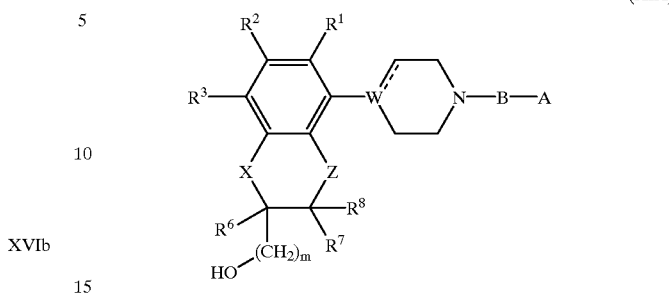

wherein $R^1$–$R^3$, $R^6$–$R^8$, A, B, X, Z, W, and the dotted line are as defined above, and m=0–4, in order to obtain the corresponding carboxylic acid derivatives;

q) hydrolysis and/or reduction of the carboxylic function of compounds of formula XX, (XX)

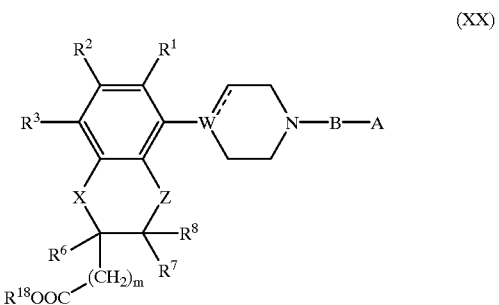

wherein $R^1$–$R^3$, $R^6$–$R^8$, $R^{18}$, A, B, X, Z, W, and the dotted line are as defined above, and m=0–4, in order to get the corresponding carboxylic acids or alcohols, respectively;

whereupon the compounds of formula (I) are isolated as the free base or in the form of a pharmaceutically acceptable salt thereof.

The reduction according to method a) is preferably carried out in an inert organic solvent such as diethyl ether or tetrahydrofuran in the presence of lithium aluminium hydride at reflux temperature. Starting compounds of formula (V), in which A is 3-indolyls, are generally prepared from reagents of formula (VI), 1,3-unsubstituted indoles, and oxalyl chloride according to known literature procedures.

The alkylation according to method b) is conveniently performed in an inert organic solvent such as a suitably boiling alcohol or ketone, preferably in the presence of a base (potassium carbonate or triethylamine) at reflux temperature. Arylpiperazine derivatives of formula (VI) are conveniently prepared from the corresponding arylamine according to the method described by Martin et al, *J. Med. Chem.*, 1989, 32, 1052, or the method described by Kruse et al, *Rec. Trav. Chim. Pays-Bas,* 1988, 107, 303. The starting arylamines are either commercially available or are well described in the literature.

Aryltetrahydropyridine derivatives of formula (VI) are known from literature, cf. U.S. Pat. No. 2,891,066; McElvain et al, *J. Amer. Chem. Soc.* 1959, 72, 3134. Conveniently, the corresponding arylbromide is lithiated with BuLi followed by addition of 1-benzyl-4-piperidone. Subsequent treatment with acid gives the N-benzyl-aryltetrahydropyridine. The benzyl group can be removed by catalytic hydrogenation or by treatment with e.g. ethyl chloroformate to give the corresponding ethyl carbamate followed by acidic or alkaline hydrolysis. The starting arylbromides are either commercially available or well described in the literature.

Reagents of formula L—B—A are either commercially available or can be prepared by literature methods, e.g. from the corresponding carboxylic acid derivative by reduction to the hydroxy derivatives and conversion of the hydroxy group to the group L by conventional methods.

The reductive alkylation according to method c) is performed by standard literature methods. The reaction can be performed in two steps, i.e. coupling of (VI) and the reagent of formula L—B—A by standard methods via the carboxylic acid chloride or by use of coupling reagents such as e.g. dicyclohexylcarbodiimide followed by reduction of the resulting amide with lithium aluminium hydride. The reaction can also be performed by a standard one-pot procedure. Carboxylic acids or aldehydes of formula K—B'—A are either commercially available or described in the literature.

Reduction of the double bonds according to method d) is conveniently performed by treatment with diborane or a diborane precursor such as the trimethylamine or dimethylsulfide complex in an inert solvent such as e.g. tetrahydrofuran or dioxane from 0° C. to reflux temperature followed by acid catalyzed hydrolysis of the intermediate borane derivative. The reduction can alternatively be performed by treatment with sodium cyanoborohydride in trifluoroacetic acid, by use of magnesium metal, or by catalytic hydrogenation.

Reduction of the double bonds according to methods e) and f) is most conveniently performed by hydrogenation in an alcohol in the presence of a noble metal catalyst, such as e.g. platinum or palladium.

The removal of halogen substituents according to method g) is conveniently performed by catalytic hydrogenation in an alcohol in the presence of a palladium catalyst or by treatment with ammonium formate in an alcohol at elevated temperatures in the presence of a palladium catalyst.

The dialkylation of amines according to methods h) and i) is most conveniently performed at elevated temperatures in an inert solvent such as e.g. chlorobenzene, toluene, N-methylpyrrolidone, dimethylformamide, or acetonitrile. The reaction might be performed in the presence of base such as e.g. potassium carbonate or triethylamine. Starting materials for processes h) and i) are commercially available or can be prepared from commercially available materials using conventional methods.

The N-alkylation according to method j) is performed in an inert solvent. e.g. an alcohol or ketone, at elevated temperatures in the presence of base, e.g. potassium carbonate or triethylamine, at reflux temperature. Alternatively, a phase-transfer reagent can be used.

The addition of for example a substituted vicinal dihalo derivative according to method k) by refluxing XIV in a solvent, inert to the selected reaction conditions (e.g. ketones, benzene or alcohol), in the presence of a base, e.g. potassium carbonate, triethylamine or sodium hydroxide in the presence of a phase transfer reagent (Koo, et al., *J. Am. Chem. Soc.* 1955, 77,5373–5375, Stillings, et al., *J. Med. Chem.* 1985, 28,1054–1062, Dzvinchuk, et al., *Tetrahedron* 1986, 386–389).

Cyclization of keto compounds according to methods l) or m) is performed, by either base treatment or by employing acidic conditions (See references above in method k, or Thiéry, et al, *Tetrahedron* 1997, 53 (6), 2061–2974).

Substitution according to method n) can be performed using a Lewis acid. e.g., borontrifluoride etherate or trimethylsilyl trifluoromethanesulphonate and an activated nucleophile (trimethylsilylated compounds). (Stillings, et al., *J. Med. Chem.* 1985, 28,1054–1062, Thiéry, et al., *Tetrahedron* 1997, 53 (6), 2061–2974).

Reactions according to method o) is performed by use of standard conditions for nitrile hydrolysis and reductions according to method o) is conveniently performed in an inert solvent such as e.g., diethyl ether or tetrahydrofuran using lithium aluminium hydride or alane.

Oxidation according to method p) can be performed by using potassium pergamanate in a sodium carbonate solution (A. Salimbeni & E. Manghisi. *J. Heterocyclic Chem.* 1980, 17:489–492).

Reduction according to method q) can be performed using lithium aluminium hydride in anhydrous diethyl ether or tetrahydrofuran (Koo, et al., *J. Am. Chem. Soc.* 1955, 77:5373–5375).

The following examples will illustrate the invention further. They are, however, not to be construed as limiting.

EXAMPLES

Melting points were determined on a Büchi B-540 apparatus and are uncorrected. Mass spectra were obtained on a Quattro MS-MS system from VG Biotech, Fisons Instruments or on a Sciex API 150EX from Perkin Elmer. Spectra were obtained at two sets of operating conditions using electrospray ionisation: one set to obtain molecular weight information (MH+, 20 eV) and the other set to induce fragmentation patterns (70–100 eV). The background was substracted. The relative intensities of the ions are obtained from the fragmentation pattern. When no intensity is indicated for the molecular ion (MH+) this ion was only present under the first set of operating conditions. $^1$H NMR spectra were recorded at 250 MHz on a Bruker AC 250 or at 500 MHz on a Bruker DRX 500. Deuterated chloroform (99.8% D) or dimethylsulfoxide (99.9% D) were used as solvents. TMS was used as internal reference standard. Chemical shifts are expressed as ppm values. The following abbreviations are used for multiplicity of NMR signals: s=singlet, d=doublet, t=triplet, q=quartet, qv=quintet, h=heptet, dd=double doublet, dt=double triplet, dq=double quartet, tt=triplet of triplets, m=multiplet, b=broad. NMR signals corresponding to acidic protons are to some extent omitted. Content of water in crystalline compounds were determined by Karl Fischer titration. Proper elemental analysis for all target compounds were obtained. Standard work-up procedures refer to extraction with the indicated organic solvent from proper aqueous solutions, drying of combined organic extracts (anhydrous $MgSO_4$ or $NaSO_4$), filtering, and evaporation of the solvent in vacuo. For column chromatography silica gel of type Kieselgel 60, 40–60 mesh ASTM was used.

Example 1

1a, 1-[1,4-Benzodioxan-5-yl]-4-[1-(inden-1-yl)-4-butyl] piperazine, oxalate

A mixture of 4-(1-indenyl)butyl methanesulfonate (1.2 g, prepared as described in U.S. Pat. No. 5,665,725), 1-(1,4-benzodioxan-5-yl)piperazine (1.2 g), and potassium carbonate (0.8 g) in 3-methyl-2-pentanone (50 mL) was refluxed for 16 h. Cooling, filtration, and removal of solvent in vacuo gave an oil which was applied to silica gel flash chromatography (eluent: heptane/methylene chloride/triethylamine 70:26:4). The obtained oil was converted to the title oxalate salt (0.7 g) from acetone by addition of oxalic acid. Mp 130–31° C. $^1$H NMR (DMSO-$d_6$): 1.60–1.90 (m, 4H); 2.55 (t, 2H); 3.05 (t, 2H); 3.15 (s, 8H); 3.35 (s, 2H); 4.15–4.35 (m, 4H); 6.30 (s, 1H); 6.50 (t, 1H); 6.60 (s, 1H); 6.75 (t, 1H); 7.20 (t. 1H); 7.25 (t. 1H); 7.40 (d, 1H); 7.50 (d, 1H). MS m/z (%): 391 (MH+, 79%), 218 (37%), 162 (50%), 129 (100%)

The following compounds were prepared analogously (see U.S. Pat. No. 5,665,725 for preparation of corresponding methanesulfonates):

1b, 1-[1,4-Benzodioxan-5-yl]-4-[1-(indan-1-yl)-1-buten-4-yl]piperazine, oxalate

Mp 154–57° C. $^1$H NMR (DMSO-$d_6$): 1.60–1.90 (m, 1H); 2.15–2.35 (m, 1H); 2.35–2.50 (m, 2H); 2.70–3.00 (m, 2H); 3.05 (t, 2H); 3.20 (s, 8H); 3.70 (q, 1H); 4.25 (s, 8H); 5.50–5.60 (m, 2H); 6.50 (d, 1H); 6.55 (d, 1H); 6.75 (t, 1H); 7.00–7.20 (m, 3H); 7.20–7.30 (m, 1H). MS m/z (%): 391 (MH+, 62%), 233 (27%), 178 (31%), 129 (100%).

1c, 1-[1,4-Benzodioxan-5-yl]-4-[1-(indan-1-yl)-4-butyl]piperazine, oxalate

Mp 154–155° C. $^1$H NMR (DMSO-$d_6$): 1.25–1.50 (m, 3H), 1.55–1.95 (m, 4H); 2.10–2.30 (m, 1H); 2.65–2.90 (m, 2H); 2.90–3.10 (m, 3H); 4.10–4.35 (m, 4H); 6.50 (d, 1H); 6.55 (d, 1H); 6.75 (t, 1H); 7.00–7.15 (m, 2H); 7.15–7.25 (m, 2H). MS m/z (%): 393 (MH+, 100%), 178 (45%), 129 (34%).

Example 2

2a, 1-[1,4-Benzodioxan-5-yl]-4-[2-(5-fluorobenzofuran-3-yl)ethyl]piperazine, oxalate A solution of 5-fluorobenzofuran-3-carboxylic acid (56 g) and saturated etheral solution of hydrochloric gas (300 mL) in methanol (600 mL) was stirred for 16 h at room temperature. Further etheral HCl was added (300 mL) followed by stirring for 24 h. Concentration in vacuo gave a dark crystalline material, methyl 5-fluorobenzofuran-3-carboxylate (58 g). Lithium aluminium hydride (15 g) was suspended in tetrahydrofuran (400 mL) under a nitrogen atmosphere followed by dropwise addition of a solution of methyl 5-fluorobenzofuran-3-carboxylate (58 g) in tetrahydrofuran (300 mL). The temperature increased to 55° C. during the addition. After stirring for 2 h the reaction was quenched successively with water (30 mL), 15% aq. sodium hydroxide (15 mL), and water (75 mL). Further tetrahydrofuran (500 mL) was added and the mixture stirred for 1 h. The mixture was filtered and the precipitate extracted with a mixture of methylene chloride (1 L) and ethanol (0.5 L). The combined organic phases were concentrated in vacuo giving an oil which was applied to silica gel flash chromatography (eluent: methylene chloride/25% aq. NH$_3$ 99:1). The resulting yellow oil, 5-fluorobenzofuran-3-ylmethanol (14.4 g) crystallised on standing.

A solution of 5-fluorobenzofuran-3-ylmethanol (14 g) in methylene chloride (250 mL) was treated successively with 5 drops of dimethylformamide and thionyl chloride (28 mL). After stirring for 16 h at room temperature the reaction was concentrated in vacuo giving 3-chloromethyl-5-fluorobenzofuran as an oil (19.4 g).

A suspension of sodium cyanide (10 g) in dimethylsulfoxide (150 mL) was heated to 80° C. followed by quick addition of a solution of 3-chloromethyl-5-fluorobenzofuran (10 g) in dimethylsulfoxide (50 mL). The mixture was kept at 80° C. for ½ h and then poured onto ice. Standard work-up with diethyl ether gave a dark crystalline material, 5-fluorobenzofuran-3-ylacetonitrile (8.8 g).

A solution of 5-fluorobenzofuran-3-ylacetonitrile (8.8 g) in methanol (350 mL) was treated with a saturated etheral solution of hydrochloric gas (350 mL) and stirred for 16 h at room temperature. The mixture was concentrated in vacuo and standard work-up with diethyl ether/water gave methyl 5-fluorobenzofuran-3-ylacetate (9.4 g) as an oil.

The obtained methyl ester was dissolved in methanol (200 mL) and 6 M aq. sodium hydroxide (400 mL) was added followed by stirring for 16 h at room temperature. Organic solvent was removed in vacuo followed by acidification with 6 M hydrochloric acid. Standard work-up with ethyl acetate gave 5-fluorobenzofuran-3-ylacetic acid (9.2 g) as a crystalline material.

A mixture of 5-fluorobenzofuran-3-ylacetic acid (1.3 g), 1-(1,4-benzodioxan-5-yl)piperazine (1.7 g), N,N'-dicyclohexylcarbodiimide (1.6 g), and 4-dimethylaminopyridine (0.1 g) in dry tetrahydrofuran (100 mL) was stirred for 72 h at room temperature. Filtration, concentration in vacuo and standard work-up with ethyl acetate/aq. ammonia gave an oil. Purification by flash chromatography on silica gel (eluent: ethyl acetate/heptane/triethylamine 82:15:3 gave a yellow oil, 1-[1,4-benzodioxan-5-yl]-4-[5-fluorobenzofuran-3-yl)methylcarbonyl]piperazine (0.8 g).

The oil was dissolved in dry tetrahydrofuran (30 mL) and added dropwise to a suspension of lithium aluminium hydride (0.38 g) in dry tetrahydrofuran (70 mL) under a nitrogen atmosphere at room temperature. After reflux for 3 h the reaction was quenched by successive additions of water (0.76 mL), 15% aq. sodium hydroxide (0.38 mL), water (1.9 mL). Standard work-up gave an oil which was applied to silica gel flash chromatography (eluents: a) heptane/ethyl acetate/triethylamine 55:43:2, b) ethyl acetate/heptane/triethylamine 70:26:4). The resulting oil (0.7 g) was dissolved in ethyl acetate and addition of oxalic acid (0.17 g) and filtration gave the title oxalate as white colourless crystals. Mp 210–17° C. $^1$H NMR (DMSO-$d_6$): 3.00 (t, 2H); 3.20 (s, 8H); 4.00 (t, 2H); 4.25 (d, 4H); 6.50 (d, 1H); 6.55 (d, 1H); 6.25 (t, 1H); 7.15 (t, 1H); 7.50–7.70 (m, 2H); 8.00 (s, 1H). MS m/z (%): 383 (MH+, 8%), 233 (60%), 218 (22%), 190 (21%), 70 (100%).

The following compound was prepared analogously:

2b, 1-[1,4-Benzodioxan-5-yl]-4-[2-(6-chloroindazol-3-yl)ethyl]piperazine, oxalate.

Mp 111–13° C. $^1$H NMR (DMSO-$d_6$): 2.95–3.35 (m, 12H); 4.25 (dd, 4H); 6.50 (d, 1H); 6.55 (d, 1H); 6.75 (t, 1H); 7.15 (d, 1H); 7.55 (s, 1H); 7.85 (d, 1H). MS m/z (%): 399 (MH+, 22%), 218 (100%), 162 (45%). The starting 6-chloroindazol-3-yl acetic acid was prepared according to J. Med. Chem. 35 (1992) 2155.

Example 3

3a, 1-[Benzofuran-7-yl]-4-[2-(5-fluorobenzofuran-3-yl)ethyl]piperazine, fumarate A solution of 5-fluorobenzofuran-3-ylacetic acid (4.6 g, prepared as described in Example 2) in dry tetrahydrofuran (200 mL) was added dropwise to a suspension of lithium aluminium hydride (4.5 g) in dry tetrahydrofuran (150 mL) at room temperature. After reflux for 2 h the reaction was quenched by successive additions of water (9.2 mL), 15% aq. sodium hydroxide (4.6 mL), water (23 mL). Filtration and removal of solvent in vacuo gave an oil, 2-(5-fluorobenzofuran-3-yl)ethanol (4.3 g).

A solution of 2-(5-fluorobenzofuran-3-yl)ethanol (5.2 g) and tetrabromomethane (11.6 g) in acetonitrile (175 mL) was treated with triphenylphosphine (8.3 g) at 0° C. After stirring for 15 min, the mixture was concentrated in vacuo an the resulting oil was applied to a silica gel flash column (eluent: heptane/ethyl acetate 65:35) resulting in an oil, 3-(2-bromoethyl)-5-fluorobenzofuran (7.4 g).

A mixture of 3-(2-bromoethyl)-5-fluorobenzofuran (1.4 g), 1-(benzofuran-7-yl)piperazine (1.0 g), potassium carbonate (1.5 g), and potassium iodide (0.1 g) in 3-methyl-2-pentanone (100 mL) was refluxed for 16 h. Addition of water (100 mL) followed by standard work-up gave an oil which was applied to silica gel flash chromatography (eluent: heptane/ethyl acetate/triethylamine 80:15:5). The resulting oil was dissolved in ethanol and addition of fumaric acid gave the title fumarate as a colourless crystalline material (0.9 g). Mp 177–79° C. $^1$H NMR (DMSO-$d_6$): 2.70–2.80 (m, 6H); 2.90 (t, 2H); 3.25–3.35 (m, 4H); 6.60 (s, 2H); 6.75 (t, 1H); 6.90 (d, 1H); 7.10–7.25 (m, 3H); 7.55 (dd, 1H); 7.60 (dd, 1H); 7.90–8.00 (m, 2H). ). MS m/z (%): 365 (MH+, 5%), 215 (90%), 172 (22%), 163 (12%), 70 (100%).

The following compounds were prepared analogously:

3b, 1-[1,4-Benzodioxan-5-yl]-4-[3-(6-fluorobenzo[1,2]isoxazol-3-yl)-1-propyl]piperazine, fumarate.

Mp 187–89° C. $^1$H NMR (DMSO-$d_6$): 2.00 (qv, 2H); 2.55 (t, 2H); 2.55–2.70 (m, 4H); 2.85–3.00 (m, 4H); 3.05 (t, 2H); 4.15–4.30 (m, 4H); 6.45 (dd, 1H); 6.50 (dd, 1H); 6.60 (s, 2H); 6.75 (t, 1H); 7.25 (dt, 1H); 7.70 (dd, 1H); 8.00 (dd, 1H). MS m/z (%): 398 (MH+, 9%), 221 (7%), 177 (100%), 150 (9%). The starting 3-(6-fluorobenzo1,2]isoxazol-3-yl)-1-propyl chloride was prepared according to *Drug Design Discov.*, 1992, 8, 225.

3c, 1-[1,4-Benzodioxan-5-yl]-4-[2-(4-methylbenzofuran-3-yl)ethyl]piperazine, oxalate Mp 204–6° C. $^1$H NMR (DMSO-$d_6$): 2.65 (s, 3H); 3.10–3.40 (m, 12H); 4.25 (dd, 4H); 6.50 (d, 1H); 6.55 (d, 1H); 6.75 (t, 1H); 7.00 (d, 1H); 7.20 (t, 3H); 7.40 (d, 1H); 7.80 (s, 1H).

MS m/z (%): 379 (MH+, 20%), 233 (75%), 218 (100%), 190 (43%), 162 (85%).

3d, 1-[1,4-Benzodioxan-5-yl]-4-[2-(5-chlorobenzofuran-3-yl)ethyl]piperazine, oxalate Mp 206–8° C. $^1$H NMR (DMSO-$d_6$): 3.05 (t, 2H); 3.10–3.40 (m, 10H), 4.10–4.35 (m, 4H); 6.50 (d, 1H); 6.55 (d, 1H); 6.75 (t, 1H); 7.35 (dd, 1H); 7.65 (d, 1H); 7.85 (d, 1H); 8.00 (s, 1H). MS m/z (%): 399 (MH+, 45%), 233 (100%), 218 (77%), 190 (40%), 162 (48%).

3e, 1-[1,4-Benzodioxan-5-yl]-4-[2-(6-methylbenzofuran-3-yl)ethyl]piperazine, oxalate Mp 174–76° C. $^1$H NMR (DMSO-$d_6$): 3.00 (t 2H); 3.10–3.40 (m, 10H); 4.10–4.35 (m, 4H); 6.50 (d, 1H); 6.55 (d, 1H); 6.75 (t, 1H): 7.10 (dd, 1H); 7.35 (s, 1H); 7.60 (d, 1H); 7.80 (s, 1H). MS m/z (%): 379 (MH+, 22%), 233 (100%), 218 (61%), 162 (59%).

3f, 1-[1,4-Benzodioxan-5-yl]-4-[2-(benzofuran-3-yl)ethyl]piperazine, oxalate

Mp 206–8° C. $^1$H NMR (DMSO-$d_6$): 3.05 (t, 1H), 3.10–3.40 (m, 10H); 4.10–4.35 (m, 4H); 6.50 (d, 1H); 6.55 (d, 1H); 6.75 (t, 1H); 7.20–7.40 (m, 2H); 7.55 (dd, 1H); 7.75 (dd, 1H); 7.90 (s, 1H). MS m/z (%): 365 (MH+, 41%), 233 (100%), 218 (96%), 190 (61%), 162 (87%).

3g, 1-[2-(5-chlorobenzofuran-3-yl)ethyl]-4-[2,3-dihydrobenzofuran-7-yl]-1,2,3,6-tetrahydropyridine, oxalate Mp 187–202° C. $^1$H NMR (DMSO-$d_6$): 2.75 (s, 1H); 3.15 (t, 2H); 3.20 (t, 2H); 3.25–3.45 (m, 4H); 3.85 (s, 2H); 4.60 (t, 2H); 6.35 (s, 1H); 6.85 (t, 1H); 7.10 (d, 1H); 7.20 (d, 1H); 7.35 (d, 1H); 7.60 (d, 1H); 7.85 (s, 1H); 8.00 (s, 1H). MS m/z (%): 380 (MH+, 14%), 179 (90%), 144 (59%), 115 (100%).

3h, 4-[Benzofuran-7-yl]-1-[2-(5-fluorobenzofuran-3-yl)ethyl]-1,2,3,6-tetrahydropyridine, oxalate Mp 201–11° C. $^1$H NMR (DMSO-$d_6$): 2.90 (s, 2H); 3.15 (t, 2H); 3.35 (t, 2H); 3.40–3.50 (m, 2H); 3.95 (s, 2H); 6.65 (s, 1H); 7.00 (s, 1H); 7.20 (dt, 1H); 7.30 (t, 1H); 7.35 (d, 1H); 7.55–7.65 (m, 3); 8.00 (s, 1H); 8.05 (s, 1H). MS m/z (%): 362 (MH+, 18%), 192 (22%), 163 (83%), 135 (92%), 115 (100%).

3i, 1-[1,4-Benzodioxan-5-yl]-4-[2-(7-chlorobenzofuran-3-yl)ethyl]piperazine, oxalate Mp 190–92° C. $^1$H NMR (DMSO-$d_6$): 2.95–3.35 (m, 12H); 4.15–4.30 (m, 4H); 6.50 (d, 1H); 6.55 (d, 1H); 6.75 (t, 1H); 7.35 (t, 1H); 7.45 (d, 1H); 7.75 (d, 1H); 8.00 (s, 1H). MS m/z (%): 399 (MH+), 233 (100%), 218 (49%), 162 (49%), 116 (69%).

Example 4

4a, 1-[1,4-Benzodioxan-5-yl]-4-[3-(7-chloro-4-methylbenzofuran-3-yl)-1-propyl]piperazine, oxalate Malonic acid diethyl ester (8.5 g) was dissolved in dimethylformamide (75 mL) followed by addition of potassium tert-butoxide (5.9 g). After stirring for 15 min at room temperature, a solution of 3-chloromethyl-7-chloro-4-methylbenzofuran (3.8 g, prepared analogously to the 5-fluoro analogue as described in Example, 2) in dimethylformamide (25 mL) was added dropwise. After stirring for 2 hours the reaction mixture was poured onto ice-water. Standard work-up with acetyl acetate gave a yellow oil (10 g) of diethyl 2-(7-chloro-4-methylbenzofuran-3-yl)malonate, sufficiently pure for further synthesis.

A portion of this product (6.0 g) was dissolved in acetone (50 mL) and stirred for 5 min followed by addition of water (50 mL) and conc. hydrochloric acid (50 mL). After reflux for 16 hours, the reaction mixture was cooled to room temperature and extracted with ethyl acetate. Standard washing procedure with ammonia and 2 M hydrochloric acid, drying of the organic phase over magnesium sulfate, filtration and removal of solvent in vacuo gave 3-(7-chloro-4-methylbenzofuran-3-yl)propionic acid (2.5 g) as a colorless solid. Treatment of this solid (2.5 g) with thionyl chloride (12 g) in methylene chloride and 1 drop of dimethylformamide at reflux for 3 hours followed by concentration of the reaction mixture in vacuo gave 3-(7-chloro-4-methylbenzofuran-3-yl)propionyl chloride (2.7 g) as a brown oil.

The oil was dissolved in trichloroethane (25 mL) and added dropwise to a mixture of 1-(benzodioxane-5-yl)piperazine (1.9 g) and triethylamine (10 mL) in trichloroethane (75 mL) over 15 min at room temperature. After reflux for 16 hours, the reaction mixture was concentrated in vacuo and the resulting oil applied to silica gel flash chromatography (eluent: ethyl acetate/heptane/triethylamine 15:4:1) giving 1-(benzodioxane-5-yl)-4-[2-(7-chloro-4-methylbenzofuran-3-yl)ethylcarbonyl]piperazine (2.1 g) as a yellow oil. The product was dissolved in dry tetrahydrofuran (25 mL) and added dropwise to a suspension of lithium aluminium hydride (1.5 g) in dry tetrahydrofuran (75 mL). The mixture was stirred for 45 min at room temperature. The mixture was quenched by successive addition of water (1 mL), 15% sodium hydroxide (0.5 mL), and water (1.5 mL). After stirring for 2 hours, the mixture was filtered and concentrated in vacuo. The resulting oil was applied to flash chromatography (eluent: ethyl acetate/heptane 1:1) giving the title compound which was crystallised as the fumarate salt (0.7 g) from acetone.

Mp 178–81° C. $^1$H NMR (DMSO-$d_6$): 2.00 (qv, 2H); 2.60 (s, 3H); 2.85 (t, 2H); 3.10 (t, 2H); 3.15 (broad s, 8H); 4.15–4.35 (m, 4H); 6.50 (d, 1H); 6.55 (d, 1H); 6.75 (t 1H); 7.05 (d, 1H); 7.25 (d, 1H); 7.90 (s, 1H).

MS m/z (%): 427 (MH+, 100%), 218 (43%), 178 (71%), 122 (80%).

The following compounds were prepared analogously:

4b, 1-[1,4-Benzodioxan-5-yl]-4-[3-(7-chloro-benzofuran-3-yl)-1-Propyl]Piperazine, fumarate $^1$H NMR (DMSO-$d_6$): 1.85 (qv, 2H); 2.40 (t, 2H); 2.55 (broad s, 4H); 2.70 (t, 2H); 3.00 (broad s, 4H); 4.10–4.30 (m, 4H); 6.45 (d, 1H); 6.50 (d, 1H); 6.60 (s, 1H); 6.70 (t, 1H); 7.25 (t, 1H); 7.40 (d, 1H); 7.65 (d, 1H); 7.90 (s, 1H).

MS m/z (%): 413 (41%), 218 (10%), 178 (100%), 122 (62%).

4c 1-[3-(7-Chlorobenzofuran-3-yl)-1-propyl]-4-[8-cyano-1,4-benzodioxan-5-yl]piperazine, fumarate $^1$H NMR (DMSO-$d_6$): 1.85 (qv, 2H); 2.40 (t, 2H); 2.55 (broad s, 4H); 2.70 (t, 2H); 3.10 (broad s, 4H); 4.25–4.35 (m, 2H); 4.35–4.45 (m, 2H); 6.55 (d, 1H); 6.60 (s, 1H); 7.20 (d, 1H); 7.30 (t, 1H); 7.40 (d, 1H); 7.65 (d, 1H); 7.95 (s, 1H).

MS m/z (%): 438 (MH+, 73%), 243 (100%), 203 (68%), 165 (84%).

Example 5

5a, 1-[1,4-Benzodioxan-5-yl]-4-[3-(4-methylbenzofuran-3-yl)-1-propyl]piperazine, oxalate A mixture of 4a (0.6 g), palladium on charcoal (5%, 0.6 g), 2 M sodium hydroxide solution (2 mL) and methanol (50 mL) was hydrogenated in a Parr apparatus at 3 atm of hydrogen pressure for 1.5 hours. Filtration, addition of ethyl acetate, washing with water, and removal of solvents in vacuo gave the title compound as a yellow oil which was crystallised as the fumarate salt (0.4 g) from acetone.

Mp 212–14° C. $^1$H NMR (DMSO-$d_6$): 2.05 (qv, 2H); 2.55 (s, 31H); 2.85 (t, 2H); 3.10 (t, 2H); 3.20 (broad s, 2H); 4.10–4.30 (m, 4H); 6.50 (d, 1H); 6.55 (d, 1H); 6.75 (t, 1H); 7.00 (d, 1H); 7.20 (t, 1H); 7.85 (d, 1H); 7.75 (s, 1H).

MS m/z (%): 393 (MH+, 32%), 218 (45%), 178 (60%), 189 (100%).

Pharmacological Testing

The affinity of the compounds of the invention to 5-$HT_{1A}$ receptors was determined by measuring the inhibition of binding of a radioactive ligand at 5-$HT_{1A}$ receptors as described in the following test:

Inhibition of $^3$H-5-CT Binding to Human 5-$HT_{1A}$ Receptors.

By this method the inhibition by drugs of the binding of the 5-$HT_{1A}$ agonist $^3$H-5-carboxamido tryptamine ($^3$H-5-CT) to cloned human 5-$HT_{1A}$ receptors stably expressed in transfected HeLa cells (HA7) (Fargin, A. et al, *J. Biol. Chem.*, 1989, 264, 14848) is determined in vitro. The assay was performed as a modification of the method described by Harrington, M. A. et al, *J. Pharmacol. Exp. Ther.*, 1994, 268, 1098. Human 5-$HT_{1A}$ receptors (40 µg of cell homogenate) were incubated for 15 minutes at 37° C. in 50 mM Tris buffer at pH 7.7 in the presence of $^3$H-5-CT. Non-specific binding was determined by including 10 µM of metergoline. The reaction was terminated by rapid filtration through Unifilter GF/B filters on a Tomtec Cell Harvester. Filters were counted in a Packard Top Counter. The results obtained are presented in table 1:

TABLE 1

| Compound No. | Inhibition of $^3$H-5-CT binding $IC_{50}$ (nM) |
|---|---|
| 1a | 1.7 |
| 1b | 6.1 |
| 1c | 2.5 |
| 2a | 14 |
| 2b | 9.3 |
| 3a | 29 |
| 3b | 7.5 |
| 3c | 19 |
| 3d | 18 |
| 3e | 8.8 |
| 3f | 8.3 |
| 3g | 24 |
| 3h | 11 |
| 3i | 2.1 |
| 5a | 2.9 |
| Pindolol* | 100 |

*reference compound

The compounds of the invention have also been tested for their effect on re-uptake of serotonin in the following test:

Inhibition of $^3$H-5-HT Uptake Into Rat Brain Synaptosomes.

Using this method, the ability of drugs to inhibit the accumulation of $^3$H-5-HT into whole rat brain synaptosomes is determined in vitro. The assay was performed as described by Hyttel, J., *Psychopharmacology* 1978, 60, 13. The results obtained are presented in table 2:

TABLE 2

| Compound No | Inhibition of serotonin reuptake $IC_{50}$ (nM) |
|---|---|
| 1a | 61 |
| 1c | 130 |
| 2a | 0.69 |
| 2b | 160 |
| 3a | 170 |
| 3b | 240 |
| 3c | 11 |
| 3d | 34 |
| 3e | 58 |
| 3f | 12 |
| 3g | 160 |
| 3h | 43 |
| 3i | 1.5 |
| 4a | 32 |
| 5a | 15 |
| Paroxetine* | 0.29 |

*reference compound

The 5-$HT_{1A}$ antagonistic activity of some of the compounds of the invention has been estimated in vitro at cloned 5-$HT_{1A}$ receptors stably expressed in transfected HeLa cells (HA7). In this test 5-$HT_{1A}$ antagonistic activity is estimated by measuring the ability of the compounds to antagonize the 5-HT induced inhibition of forskolin induced cAMP accumulation. The assay was performed as a modification of the method described by Pauwels, P. J. et al, *Biochem. Pharmacol.* 1993, 45, 375. The results obtained are presented in table 3:

TABLE 3

| Compound No. | Antagonism of Inhibition of forskolin induced cAMP accumulation $IC_{50}$ (nM) |
|---|---|
| 1a | 170 |
| 2a | 100 |
| 3b | 74 |
| 3c | 2300 |
| 3d | 550 |
| 3e | 1400 |
| 3f | 290 |
| 3i | 1500 |
| 4a | 260 |
| 5a | 390 |
| Pindolol* | 270 |

*reference compound

Some of the compounds of the invention have also been tested for their in vivo effect on 5-$HT_{1A}$ receptors in the assay described by Sanchez. C. Et al., *Eur. J. Pharmacol.*, 1996, 315, pp 245. In this test, antagonistic effects of test compounds are determined by measuring the ability of the test compounds to inhibit 5-MeO-DMT induced 5-HT syndrome.

The compounds of the present invention possess valuable activity as serotonin re-uptake inhibitors and have antagonistic effect at 5-$HT_{1A}$ receptors. The compounds of the invention are therefore considered useful for the treatment of diseases and disorders responsive to the inhibition of serotonin re-uptake and antagonistic activity at 5-$HT_{1A}$ receptors. Diseases responsive to the inhibition of serotonin re-uptake are well known in the art and include affective disorders, such as depression, psychosis, anxiety disorders including general anxiety disorder, panic disorder, obsessive compulsive disorder, etc.

As explained above, the antagonistic activity at 5-$HT_{1A}$ receptors of the compounds of the invention will counteract the negative feed back mechanism induced by the inhibition of serotonin reuptake and is thereby expected to improve the effect of the serotonin reuptake inhibiting activity of the compounds of the invention.

The compounds as claimed herein are therefore considered to be particularly useful as fast onset of action medicaments for the treatment of depression. The compounds may also be useful for the treatment of depressions which are non-responsive to currently available SSRIs.

Pharmaceutical Formulation

The pharmaceutical formulations of the invention may be prepared by conventional methods in the art. For example: Tablets may be prepared bar mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used.

Conveniently, the compounds of the invention are administered in unit dosage form containing said compounds in an amount of about 0.01 to 1000 mg. The total daily dose is usually in the range of about 0.05–500 mg, and most preferably about 0.1 to 50 mg of the active compound of the invention.

What is claimed is:

1. A compound of formula:

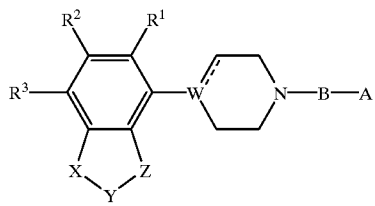

(I)

or any of its enantiomers or any mixtures thereof, or an acid addition salt thereof, wherein B is $C_{1-10}$-alkylene, $C_{2-10}$-alkenylene or $C_{2-10}$-alkynylene;

X is —O—, —S—, or —$CR^4R^5$—; and

Y is —$CR^6R^7$—, —$CR^6R^7$—$CR^8R^9$—, or —$CR^6$=$CR^7$—; or

X and Y together form a group —$CR^4$=$CR^5$—, or —$CR^4$=$CR^5$—$CR^6R^7$—;

Z is —O— or —S—;

W is N;

$R^4$, $R^5$, $R^6$, $R^7$, $R^8$ and $R^9$ are each independently selected from hydrogen, halogen, trifluoromethyl, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, $C_{1-6}$-alkoxy, $C_{1-6}$-alkylthio, amino, $C_{1-6}$-alkylamino, $C_{1-6}$-dialkylamino, phenylamino or phenyl-$C_{1-6}$-alkylamino, acylamino, hydroxy, —SH, cyano, nitro, —$COOR^{18}$, —$SO_2$—$R^{19}$ and $C_{1-6}$-alkyl substituted with a substituent selected from halogen, $C_{1-6}$-alkoxy, $C_{1-6}$-alkylthio, amino, $C_{1-6}$-alkylamino, $C_{1-6}$-dialkylamino, acylamino, hydroxy, —SH, cyano, nitro, —$COOR^{18}$ and —$SO_2$—$R^{19}$;

$R^{18}$ is hydrogen, $C_{1-6}$-alkyl, $C_{2-6}$-alkenyl, $C_{2-6}$-alkynyl, phenyl or phenyl-$C_{1-6}$-alkyl, amino, $C_{1-6}$-alkylamino or $C_{1-6}$-dialkylamino, and $R^{19}$ is $C_{1-6}$-alkyl, amino, $C_{1-6}$-alkylamino, $C_{1-6}$-dialkylamino, phenyl or phenyl-$C_{1-6}$-alkyl;

A is

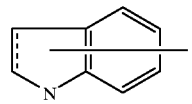

(If)

which is attached to the remainder of the compound of formula (I) via a carbon atom or a nitrogen atom in any of the two rings and wherein the dotted line is an optional bond, $E^6$ is O, and wherein any of the carbon atoms in the ring may be substituted with any of the substituents defined for $R^{12}$–$R^{17}$ below;

$R^1$, $R^2$, $R^3$, $R^{12}$, $R^{13}$, $R^{14}$, $R^{15}$, $R^{16}$ and $R^{17}$ are each independently selected from hydrogen, halogen, trifluoromethyl, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, $C_{1-6}$-alkoxy, hydroxy, formyl, acyl, amino, $C_{1-6}$-alkylamino, $C_{1-6}$-dialkylamino, acylamino, $C_{1-6}$-alkoxycarbonylamino, aminocarbonylamino, $C_{1-6}$-alkylaminocarbonylamino, $C_{1-6}$-dialkylaminocarbonylamino, nitro, cyano and —$SO_2$—$R^{19}$;

provided that when any $R^1$, $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$ or $R^{19}$ is a phenyl group or has a phenyl moiety, said phenyl group or phenyl moiety is optionally substituted with one or more substituents selected from the group consisting of halogen, trifluoromethyl, cyano, nitro, amino, $C_{1-6}$ alkylamino, $C_{1-6}$ dialkylamino, $C_{1-6}$ alkyl, $C_{1-6}$ alkoxy and hydroxy.

2. A compound according to claim 1, wherein A is attached to the remainder of the derivative of formula (I) via position 3 in the five-membered ring.

3. A compound according to claim 1, wherein

B is $C_{1-6}$ alkylene, $C_{2-6}$-alkenylene, or $C_{2-6}$-alkynylene;

X is —O— or —S—; and

Y is $CR^6R^7$—, $CR^6R^7$—$CR^8R^9$—, or —$CR^6$=$CR^7$—; and

Z is —O— or —S—;

W is N, C, or CH;

$R^6$, $R^7$, $R^8$ and $R^9$ are each independently selected from hydrogen, halogen, trifluoromethyl, $C_{1-6}$-alkyl, $C_{1-6}$-alkoxy, $C_{1-6}$-alkylthio, amino, $C_{1-6}$-alkylamino, $C_{1-6}$-dialkylamino, hydroxy, cyano, nitro, —$COOR^{18}$, —$SO_2$—$R^{19}$ and phenylamino or phenyl-$C_{1-6}$-alkylamino wherein the phenyl group may be substituted with one or more substituents selected from the group consisting of halogen, trifluoromethyl, cyano, nitro, amino, $C_{1-6}$ alkylamino, $C_{1-6}$ dialkylamino, $C_{1-6}$ alkyl, $C_{1-6}$ alkoxy and hydroxy and $C_{1-6}$-alkyl substituted with halogen, $C_{1-6}$-alkoxy, $C_{1-6}$-alkylthio, amino, $C_{1-6}$-alkylamino, $C_{1-6}$ dialkylamino, acylamino, hydroxy, cyano, nitro, —COOR$^{18}$ or —SO$_2$—R$^{19}$;

R$^{18}$ is hydrogen, $C_{1-6}$-alkyl, amino, $C_{1-6}$-alkylamino or $C_{1-6}$-dialkylamino;

R$^{19}$ is $C_{1-6}$-alkyl, amino, $C_{1-6}$-alkylamino or $C_{1-6}$-dialkylamino; and R$^1$, R$^2$, R$^3$, R$^{12}$, R$^{13}$, R$^{14}$, R$^{15}$, R$^{16}$ and R$^{17}$ are each independently selected from hydrogen, halogen, trifluoromethyl, $C_{1-6}$-alkyl, $C_{1-6}$-alkoxy, hydroxy, amino, $C_{1-6}$-alkylamino, $C_{1-6}$ dialkylamino, nitro and cyano.

4. A compound according to claim 1, which is selected from
1-[1,4-Benzodioxan-5-yl]-4-[2-(5-fluorobenzofuran-3-yl) ethyl]piperazine,
1-[Benzofuran-7-yl]-4-[2-(5-fluorobenzofuran-3-yl)ethyl] piperazine,
1-[1,4-Benzodioxan-5-yl]-4-[2-(4-methylbenzofuran-3-yl) ethyl]piperazine,
1-[1,4-Benzodioxan-5-yl]-4-[2-(5-chlorobenzofuran-3-yl) ethyl]piperazine,
1-[1,4-Benzodioxan-5-yl]-4-[2-(6-methylbenzofuran-3-yl) ethyl]piperazine,
1-[1,4-Benzodioxan-5-yl]-4-[2-(benzofuran-3-yl)ethyl] piperazine,
1-[1,4-Benzodioxan-5-yl]-4-[2-(7-chlorobenzofuran-3-yl) ethyl]piperazine,
1-[1,4-Benzodioxan-5-yl]-4-[3-(7-chlorobenzofuran-3-yl)-1-propyl]piperazine,
1-[8-Cyano-1,4-benzodioxan-5-yl]-4-[3-(7-chlorobenzofuran-3-yl)propyl]piperazine,
1-[1,4-Benzodioxan-5-yl]-4-[3-(7-chloro-4-methylbenzofuran-3-yl)-1-propyl]piperazine,
1-[1,4-Benzodioxan-5-yl]-4-[3-(4-methylbenzofuran-3-yl)-1-propyl]piperazine,
1-[1,4-Benzodioxan-5-yl]-4-[2-(6-bromobenzofuran-3-yl) ethyl]piperazine,
1-[1,4-Benzodioxan-5-yl]-4-[3-(4-chlorobenzofuran-3-yl)-1-propyl]piperazine,
1-[1,4-Benzodioxan-5-yl]-4-[4-(4-methylbenzofuran-3-yl)-1-butyl]piperazine,
1-[1,4-Benzodioxan-5-yl]-4-[4-(4-chlorobenzofuran-3-yl)-1-butyl]piperazine,
1-[1,4-Benzodioxan-5-yl]-4-[4-(7-chlorobenzofuran-3-yl)-1-butyl]piperazine,
or a pharmaceutically acceptable acid addition salt thereof.

5. A compound of formula:

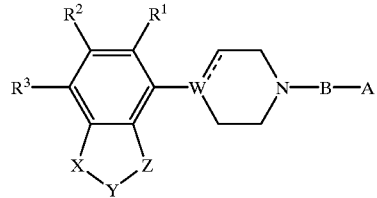

(I)

or any of its enantiomers or any mixtures thereof, or an acid addition salt thereof, wherein B is $C_{1-10}$-alkylene, $C_{2-10}$-alkenylene or $C_{2-10}$-alkynylene;

X is —O—, —S—, or —CR$^4$R$^5$—; and

Y is —CR$^6$R$^7$—, —CR$^6$R$^7$—CR$^8$R$^9$—, or —CR$^6$═CR$^7$—; or

X and Y together form a group —CR$^4$═CR$^5$—, or —CR$^4$═CR$^5$—CR$^6$R$^7$—;

Z is —O— or —S—;

W is N;

R$^4$, R$^5$, R$^6$, R$^7$, R$^8$ and R$^9$ are each independently selected from hydrogen, halogen, trifluoromethyl, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, $C_{1-6}$-alkoxy, $C_{1-6}$-alkylthio, amino, $C_{1-6}$-alkylamino, $C_{1-6}$-dialkylamino, phenylamino or phenyl-$C_{1-6}$-alkylamino, acylamino, hydroxy, —SH, cyano, nitro, —COOR$^{18}$, —SO$_2$—R$^{19}$ and $C_{1-6}$-alkyl substituted with a substituent selected from halogen, $C_{1-6}$-alkoxy, $C_{1-6}$-alkylthio, amino, $C_{1-6}$-alkylamino, $C_{1-6}$-dialkylamino, acylamino, hydroxy, —SH, cyano, nitro, —COOR$^{18}$ and —SO$_2$—R$^{19}$;

R$^{18}$ is hydrogen, $C_{1-6}$-alkyl, $C_{2-6}$-alkenyl, $C_{2-6}$-alkynyl, phenyl or phenyl-$C_{1-6}$-alkyl, amino, $C_{1-6}$-alkylamino or $C_{1-6}$-dialkylamino, and R$^{19}$ is $C_{1-6}$-alkyl, amino, $C_{1-6}$-alkylamino, $C_{1-6}$-dialkylamino, phenyl or phenyl-$C_{1-6}$-alkyl;

A is

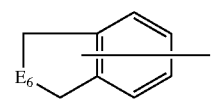

(Ij)

which is attached to the remainder of the compound of formula (I) via a carbon atom or a nitrogen atom in any of the two rings wherein E$^6$ is O or S, and wherein any of the carbon atoms in the ring may be substituted with any of the substituents defined for R$^{12}$–R$^{17}$ below;

R$^1$, R$^2$, R$^3$, R$^{12}$, R$^{13}$, R$^{14}$, R$^{15}$, R$^{16}$ and R$^{17}$ are each independently selected from hydrogen, halogen, trifluoromethyl, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, $C_{1-6}$-alkoxy, hydroxy, formyl, acyl, amino, $C_{1-6}$-alkylamino, $C_{1-6}$-dialkylamino, acylamino, $C_{1-6}$-alkoxycarbonylamino, aminocarbonylamino, $C_{1-6}$-alkylaminocarbonylamino, $C_{1-6}$-dialkylaminocarbonylamino, nitro, cyano and —SO$_2$—R$^{19}$;

provided that when any R$^1$, R$^2$, R$^3$, R$^4$, R$^5$, R$^6$, R$^7$, R$^8$, R$^9$, R$^{12}$, R$^{13}$, R$^{14}$, R$^{15}$, R$^{16}$, R$^{17}$, R$^{18}$ or R$^{19}$ is a phenyl group or has a phenyl moiety, said phenyl group or phenyl moiety is optionally substituted with one or more substituents selected from the group consisting of halogen, trifluoromethyl, cyano, nitro, amino, $C_{1-6}$ alkylamino, $C_{1-6}$ dialkylamino, $C_{1-6}$ alkyl, $C_{1-6}$ alkoxy and hydroxy.

6. A compound according to claim 5, wherein A is attached to the remainder of the derivative of formula (I) via position 3 in the five-membered ring.

7. A compound according to claim 5, wherein

B is $C_{1-6}$ alkylene, $C_{2-6}$-alkenylene, or $C_{2-6}$-alkynylene;

X is —O— or —S—; and

Y is CR$^6$R$^7$—, CR$^6$R$^7$—CR$^8$R$^9$—, or —CR$^6$═CR$^7$—; and

Z is —O— or —S—;

W is N, C, or CH;

R$^6$, R$^7$, R$^8$ and R$^9$ are each independently selected from hydrogen, halogen, trifluoromethyl, $C_{1-6}$-alkyl, $C_{1-6}$-alkoxy, $C_{1-6}$-alkylthio, amino, $C_{1-6}$-alkylamino, $C_{1-6}$-dialkylamino, hydroxy, cyano, nitro, —COOR$^{18}$, —SO$_2$—R$^{19}$ and phenylamino or phenyl-$C_{1-6}$-alkylamino wherein the phenyl group may be substituted with one or more substituents selected from the group consisting of halogen, trifluoromethyl, cyano, nitro, amino, $C_{1-6}$ alkylamino, $C_{1-6}$ dialkylamino, $C_{1-6}$ alkyl, $C_{1-6}$ alkoxy and hydroxy and $C_{1-6}$-alkyl substituted with halogen, $C_{1-6}$-alkoxy, $C_{1-6}$-alkylthio, amino, $C_{1-6}$-alkylamino, $C_{1-6}$ dialkylamino, acylamino, hydroxy, cyano, nitro, —$COOR^{18}$ or $SO_2$—$R^{19}$;

$R^{18}$ is hydrogen, $C_{1-6}$-alkyl, amino, $C_{1-6}$-alkylamino or $C_{1-6}$-dialkylamino;

$R^{19}$ is $C_{1-6}$-alkyl, amino, $C_{1-6}$-alkylamino or $C_{1-6}$-dialkylamino; and $R^1$, $R^2$, $R^3$, $R^{12}$, $R^{13}$, $R^{14}$, $R^{15}$, $R^{16}$ and $R^{17}$ are each independently selected from hydrogen, halogen, trifluoromethyl, $C_{1-6}$-alkyl, $C_{1-6}$-alkoxy, hydroxy, amino, $C_{1-6}$-alkylamino, $C_{1-6}$ dialkylamino, nitro and cyano.

8. A pharmaceutical composition comprising a compound of claim 1 or a pharmaceutically acceptable salt thereof and at least one pharmaceutically acceptable carrier or diluent.

9. A pharmaceutical composition comprising a compound of claim 5 or a pharmaceutically acceptable salt thereof and at least one pharmaceutically acceptable carrier or diluent.

10. A method of treating affective disorders in a patient in need thereof, said method comprising administering to said patient an effective amount of a compound of claim 1 or a pharmaceutically acceptable acid addition salt thereof.

11. The method of claim 10, wherein said affective disorder is depression.

12. A method of treating psychosis in a patient in need thereof, said method comprising administering to said patient an effective amount of a compound of claim 1 or a pharmaceutically acceptable addition salt thereof.

13. A method of treating anxiety disorders in a patient in need thereof, said method comprising administering to said patient an effective amount of a compound of claim 1 or a pharmaceutically acceptable salt thereof.

14. The method of claim 13, wherein said anxiety disorders are selected from the group consisting of generalized anxiety disorder, panic disorder and obsessive compulsive disorder.

15. A method of treating affective disorders in a patient in need thereof, said method comprising administering to said patient an effective amount of a compound of claim 5 or a pharmaceutically acceptable acid addition salt thereof.

16. The method of claim 15, wherein said affective disorder is depression.

17. A method of treating psychosis in a patient in need thereof, said method comprising administering to said patient an effective amount of a compound of claim 5 or a pharmaceutically acceptable addition salt thereof.

18. A method of treating anxiety disorders in a patient in need thereof, said method comprising administering to said patient an effective amount of a compound of claim 5 or a pharmaceutically acceptable salt thereof.

19. The method of claim 18, wherein said anxiety disorders are selected from the group consisting of generalized anxiety disorder, panic disorder and obsessive compulsive disorder.

* * * * *